United States Patent
Burgholzer et al.

(10) Patent No.: US 7,798,705 B2
(45) Date of Patent: Sep. 21, 2010

(54) THERMOACOUSTIC TOMOGRAPHIC METHOD AND THERMOACOUSTIC TOMOGRAPH

(75) Inventors: Peter Burgholzer, Gallneukirchen (AT);
Markus Haltmeier, Innsbruck (AT);
Otmar Scherzer, Klosterneuburg (AT)

(73) Assignees: Upper Austrian Research GmbH, Linz (AT); Universitaet Innsbruck, Innsbruck (AT)

( * ) Notice: Subject to any disclaimer, the term of this patent is extended or adjusted under 35 U.S.C. 154(b) by 0 days.

(21) Appl. No.: 11/647,890

(22) Filed: Dec. 29, 2006

(65) Prior Publication Data
US 2007/0121697 A1     May 31, 2007

Related U.S. Application Data

(63) Continuation of application No. PCT/AT2005/000244, filed on Jun. 30, 2005.

(30) Foreign Application Priority Data

Jul. 20, 2004    (AT)    .............................. A 1229/2004

(51) Int. Cl.
A61B 6/03    (2006.01)
A61B 8/00    (2006.01)
G01K 11/00    (2006.01)
G01K 3/00    (2006.01)

(52) U.S. Cl. .................. 374/117; 374/137; 374/167; 374/141; 374/5; 374/57; 600/473; 600/438

(58) Field of Classification Search ......... 374/117–120, 374/45, 4–7, 57, 121, 122, 10, 100, 44; 378/37; 600/473, 407, 438

See application file for complete search history.

(56) References Cited

U.S. PATENT DOCUMENTS

| | | | | |
|---|---|---|---|---|
| 3,472,334 A | * | 10/1969 | Snodgrass | ..................... 367/61 |
| 4,109,523 A | * | 8/1978 | Teyssandier | ............. 73/861.31 |
| 4,337,843 A | * | 7/1982 | Wendel | ....................... 181/175 |
| 4,416,552 A | * | 11/1983 | Hessemer et al. | ........... 374/117 |
| 4,495,817 A | * | 1/1985 | Hunt et al. | .................... 73/624 |
| 4,567,769 A | * | 2/1986 | Barkhoudarian | ............. 73/643 |
| 4,950,897 A | | 8/1990 | Mandelis et al. | |
| 5,243,860 A | * | 9/1993 | Habart | ........................ 73/291 |
| 5,296,374 A | * | 3/1994 | Culshaw et al. | .......... 435/287.9 |

(Continued)

OTHER PUBLICATIONS

Haltmeier, et al., „Thermoacoustic Computed Tomography with Large Planar Receivers, Inverse Problems IOP Publishing UK, dated Oct. 2004, pp. 1663-1673.

(Continued)

*Primary Examiner*—Gail Verbitsky
(74) *Attorney, Agent, or Firm*—Laurence A. Greenberg; Werner H. Stemer; Ralph E. Locher

(57) ABSTRACT

A thermoacoustic tomographic method for imaging an object, wherein the object is thermally excited by a source and the acoustic waves from the object, which are caused by the thermal excitation, from different directions of the object are detected using at least one detector and an image of the object is reconstructed from the detected acoustic waves and the positional information, wherein the acoustic waves detected by the detector are integrated at least in one direction over a length of at least $\sqrt{8} \cdot d$, where d denotes the maximum distance from a point of the object to be imaged to the detector.

21 Claims, 3 Drawing Sheets

U.S. PATENT DOCUMENTS

| | | | |
|---|---|---|---|
| 5,301,660 A * | 4/1994 | Rattner | 604/4.01 |
| 5,463,593 A * | 10/1995 | Zanelli et al. | 367/13 |
| 5,713,356 A | 2/1998 | Kruger | |
| 5,840,023 A * | 11/1998 | Oraevsky et al. | 600/407 |
| 6,003,376 A * | 12/1999 | Burns et al. | 73/584 |
| 6,102,857 A * | 8/2000 | Kruger | 600/437 |
| 6,104,942 A * | 8/2000 | Kruger | 600/407 |
| 6,128,092 A * | 10/2000 | Levesque et al. | 356/451 |
| 6,292,682 B1 * | 9/2001 | Kruger | 600/407 |
| 6,567,688 B1 * | 5/2003 | Wang | 600/430 |
| 6,609,015 B2 * | 8/2003 | Lucassen et al. | 600/322 |
| 6,633,774 B2 | 10/2003 | Kruger | |
| 6,877,894 B2 * | 4/2005 | Vona et al. | 374/45 |
| 2002/0103517 A1 * | 8/2002 | West et al. | 607/88 |
| 2005/0277834 A1 * | 12/2005 | Patch et al. | 600/437 |
| 2005/0283071 A1 * | 12/2005 | Ripoll et al. | 600/425 |
| 2006/0012367 A1 * | 1/2006 | Meaney et al. | 324/315 |
| 2006/0225507 A1 * | 10/2006 | Paulson | 73/592 |
| 2007/0088206 A1 * | 4/2007 | Peyman et al. | 600/319 |
| 2007/0093702 A1 * | 4/2007 | Yu et al. | 600/326 |
| 2007/0299341 A1 * | 12/2007 | Wang et al. | 600/443 |
| 2009/0318802 A1 * | 12/2009 | Boyden et al. | 600/437 |

OTHER PUBLICATIONS

Pilatou, et al., "Analysis of Three-dimensional Photoacoustic Imaging of a Vascular Tree in Vitro", Review of Scientific Instruments, American Institute of Physics, dated Oct. 2003, pp. 4495-4499.

Andreev, et al., "Detection of Ultrawide-band Ultrasound Pulses in Optoacoustic Tomography", Proceedings of the SPIE—The International Society for Optical Engineering, dated 2002, pp. 1383-1390.

Andreev, et al., "Image Reconstruction in 3D Optoacoustic Tomography System with Hemispherical Transducer Array", Proceedings of the SPIE—The International Society for Optical Engineering, dated 2002, pp. 137-145.

Oberheide, et al., „Two-dimensional Detection of Optoacoustic Stress Transients, Proceedings of SPIE—The International Society for Optical Engineering, dated 2002, pp. 99-105.

Kruger, et al., „Thermoacoustic Computed Tomography—Technical Considerations, American Association of Physicists in Medicine, dated Jun. 23, 1999, pp. 1832-1837.

Kruger, et al., „Thermoacoustic CT: Imaging Principles, Optosonics Inc., pp. 1-10.

* cited by examiner

THERMOACOUSTIC TOMOGRAPHIC METHOD AND THERMOACOUSTIC TOMOGRAPH

CROSS-REFERENCE TO RELATED APPLICATIONS

This is a continuation, under 35 U.S.C. §120, of copending international application No. PCT/AT2005/000244, filed Jun. 30, 2005, which designated the United States; this application also claims the priority, under 35 U.S.C. §119, of Austrian patent application No. A 1229/2004, filed Jul. 20, 2004; the prior applications are herewith incorporated by reference in their entirety.

BACKGROUND OF THE INVENTION

Field of the Invention

The invention relates to a thermoacoustic tomographic method for imaging an object, wherein the object is thermally excited by a source and the acoustic waves from the object, which are caused by the thermal excitation, from different directions of the object are detected using at least one detector and an image of the object is reconstructed from the detected acoustic waves and the positional information.

The invention also relates to a thermoacoustic tomograph for imaging an object having at least one source for thermally exciting the object, at least one detector for detecting the acoustic waves caused by the object by virtue of the excitation, having a device for moving the object and/or the at least one detector relative to one another, and having a device for reconstructing the object from the detected acoustic waves as a function of the respective position of the object.

A wide variety of three-dimensional and two-dimensional shapes fall under the term "object."

If a semitransparent object is thermally excited using a short electromagnetic pulse, for example, the sudden thermal expansion inside the object produces a pressure distribution which triggers an acoustic wave. The sound pressure produced in the process is proportional to the spatial distribution of the absorbed electromagnetic energy. The thermoacoustic tomography reconstructs this spatial distribution in the object from the measured sound waves outside the object. Since, for example, carcinogenic tissue and healthy tissue have very different electromagnetic absorption coefficients, the thermoacoustic tomography results in good contrast when imaging these two types of tissue which could not be achieved using ultrasound methods, for example. However, there are also other fields of application besides medicine for the thermoacoustic tomography. In previous thermoacoustic tomographic methods, small acoustic detectors, ideally acoustic point detectors, are used for detecting the acoustic waves outside the object, which detectors are moved relative to the object, and finally an image of the object is reconstructed from the full set of data. All previous reconstruction methods are based on approximation models (see, for example, R. A. Kruger, D. R. Reinecke, G. A. Kruger: Thermoacoustic computed tomography—technical considerations. Medical Physics, Volume 26, Issue 9, pp. 1832-1837, 1999; R. A. Kruger, W. L. Kiser, K. D. Miller, H. E. Reynolds: Thermoacoustic CT: Imaging Principles. Proceedings SPIE 3916, pp. 150-159, 2000).

U.S. Pat. No. 5,840,023 describes an optoacoustic imaging method for medical applications, wherein the human tissue is thermally excited by means of a laser. In order to detect the acoustic waves emanating from the object, a small detector or an array of a plurality of small detectors is used. Both piezoelectric and optical detectors can be used here.

U.S. Pat. No. 6,567,688 B1 shows a thermoacoustic tomographic method, wherein biological tissue is thermally excited with the aid of microwaves and the resulting sound waves are picked up with the aid of an ultrasonic transducer. In contrast to the above patent, this is a real time scanning method and not a reconstruction method. Here, too, a relatively small detector or an array of a plurality of detectors which can be focussed synthetically is used.

U.S. Pat. No. 6,633,774 B2 describes a thermoacoustic imaging system for the examination of tissue structures, which tissue is thermally excited by an electromagnetic radiation source. A rotatable arrangement of a plurality of detectors detects the acoustic waves emanating from the object. Arrays of a plurality of small detectors are used for this purpose. The object is reconstructed approximately from the recorded data. A plurality of radiation sources which are synchronized with one another may also be provided for the excitation. Piezoelements are used as detectors.

SUMMARY OF THE INVENTION

It is accordingly an object of the invention to provide a thermoacoustic tomography method and a thermoacoustic tomography device which overcome the above-mentioned disadvantages of the heretofore-known devices and methods of this general type and which provides for an optimum image quality and resolution with acceptable outlay for the reconstruction of the image data. To this end, known reconstruction methods should be used where possible while the disadvantages of the prior art methods and systems should be avoided or reduced.

With the foregoing and other objects in view there is provided, in accordance with the invention, a thermoacoustic tomographic method for imaging an object. The method comprises the following steps:

thermally exciting the object and causing acoustic waves to emanate from the object;

detecting the acoustic waves from the object, caused by the thermal excitation, from different directions of the object using at least one detector;

integrating the acoustic waves detected by the detector at least in one direction over a length of at least $\sqrt{8} \cdot d$, where d denotes a maximum distance from a point of the object to the detector; and reconstructing an image of the object from the acoustic waves detected by the detector and positional information.

In other words, the objects according to the invention are achieved, from a method-related point of view, in that the acoustic waves detected by the detector are integrated at least in one direction over a length of at least $\sqrt{8} \cdot d$, where d denotes the maximum distance from a point of the object to be imaged to the detector. This means that in the method according to the invention, a detector is used which has a size of at least $\sqrt{8} \cdot d$ at least in one dimension such that the acoustic waves detected by the detector are integrated over this length. On account of the integration over this dimension of the detector, calculation methods enabling very high resolution can now be used to reconstruct the image of the object. The size of the detector enables the measurement of the entire sound pressure emanating from the object onto the plane including the detector.

Depending on the shape of the detector with the dimension according to the invention, different mathematical methods known from other imaging methods can be used. The detector is moved in a manner known per se about the object, or the object about the detector, and a corresponding amount of data is recorded, which finally permits a reconstruction of the object. In previous thermoacoustic tomographic methods, in contrast to the method according to the invention, the measured data at the acoustic detectors is interpreted as point measured data. This approximation implies that the resolution of the reconstruction is physically limited by the size of the detectors. This approximation can be avoided by the use of large-area integrating detectors. In this case the spatial resolution is limited only by the maximum detectable frequency of the acoustic sound waves.

A further feature of the invention provides that the acoustic waves detected by the detector are integrated in one direction over the length of at least $\sqrt{8} \cdot d$. On account of the use of linear or strip-like detectors of this type, known mathematical reconstruction methods can be used. This is due to the fact that, as opposed to flat detectors, linear detectors of this type need not be rotated in all spatial directions, but can be guided on a fixed pivot or the object can rotate about a fixed pivot.

It is, of course, likewise possible that the detectors are large-area detectors, wherein the diameter of the area is at least $\sqrt{8} \cdot d$.

Provided the detectors have a planar shape, the image of the object can be reconstructed, for example, with the aid of inverse Radon transformation. The Radon transformation is well known in digital image processing, which is why a series of calculation and inversion methods exist which facilitate a reconstruction of the image of the object. The Radon transformation is the linear integral transformation which was defined by Johann Radon in 1917 and subsequently named after him. Said Radon transformation plays a fundamental role in computer tomography for the reconstruction of two-dimensional functions from one-dimensional projections. The inversion of the three-dimensional wave equation, which is applied in point detectors for the reconstruction, can be reduced to the solution of a system of one-dimensional wave equations on account of the use of the large-area detectors according to the invention.

In the abovementioned linear detectors, combinations of various other reconstruction methods can be used.

For the reconstruction of the image of the object, the detected values of a plurality of detectors can be processed. This also reduces the measurement time, since, on account of the number of used detectors, the necessary movements of the detectors about the object or vice versa are reduced accordingly.

The method is predominantly facilitated by virtue of the fact that the at least one detector is moved about the object. It is also possible for the object to rotate or for the detectors and the object to move reciprocally with respect to one another.

Advantageously, the reconstructed image of the object is displayed on a monitor or the like.

If the acoustic waves from the object, which are caused by the thermal excitation, are detected in the ultrasound frequency range of up to several GHz, accordingly suitable detectors, such as particularly thin piezoelectric sheets or layers, can therefore be used to achieve a positional resolution in the micrometer range. The spatial resolution of the images of the object is limited only by this maximum detectable ultrasound frequency when corresponding detectors are used.

For the purpose of achieving improved measurement results, the object can also be provided with contrast agents for influencing the absorption response. Here, as in other imaging methods, contrast agents customary in medicine can be used, for example.

With the above and other objects in view there is also provided, in accordance with the invention, a thermoacoustic tomograph for imaging an object, comprising:
  at least one excitation source configured to thermally excite the object;
  at least one detector for detecting acoustic waves caused by the object upon excitation thereof by said source, said at least one detector having at least one dimension with an extent of at least $\sqrt{8} \cdot d$, where d is a maximum distance from a point of the object to be imaged to said detector;
  a movement device for moving the object and/or the at least one detector relative to one another; and
  a device connected to said at least one detector for reconstructing an image of the object from the acoustic waves detected by the at least one detector in dependence on a respective position of the object.

In other words, the objects according to the invention are also achieved by a thermoacoustic tomograph, wherein the at least one detector has, at least in one dimension, an extent of at least $\sqrt{8} \cdot d$, where d denotes the maximum distance from a point of the object to be imaged to the detector. The use of detectors of this type having a large dimension achieves the detection of the entire sound pressure caused by the object onto the plane of the detector. Therefore, known mathematical methods, such as the inverse Radon transformation, can be used for the reconstruction of the three-dimensional object, and therefore stable numerical computer algorithms can be used with, simultaneously, particularly high resolution of the reconstructed object.

The detectors can be linear or strip-like detectors here, with the length of the detector being at least $\sqrt{8} \cdot d$.

In the case of the application of elongate detectors of this type, a plurality of linear or strip-like detectors can also be arranged parallel with respect to one another.

The detector can, of course, likewise be a flat detector, with the diameter of the area being at least $\sqrt{8} \cdot d$.

If the at least one detector has a planar shape, firstly a simple design of the detectors and secondly the application of the inverse Radon transformation are made possible.

On the other hand, it is also possible that the at least one detector is curved and, for example, is in the form of a semi-cylinder, wherein, in the reconstruction method, said shape of the detector must be taken into account. The advantage of curved detectors of this type lies in the fact that they have smaller external dimensions than detectors having a planar shape, while having the same-size area. However, this renders the mathematical reconstruction methods slightly more complicated.

Advantageously, the upper cut-off frequency of the detector is several GHz. On account of such a high upper cut-off frequency, a particularly high resolution in the micrometer range is achieved.

The detector can be in the form of a piezoelectric sensor which, in accordance with the piezoelectric effect, converts the impinging sound waves directly into electric signals. Piezoelectric materials are, for example, PVDF (polyvinylidene fluoride) or ZNO (zinc oxide). Such materials are available as sheets or as layers on substrate material of particularly low thickness in the micrometer and even to the nanometer range. A good positional resolution is achieved on account of the particularly low thickness. The sheets are metallized and contact-connected and therefore can simply be connected to the downstream electronic circuits, in particular amplifiers.

It is likewise possible to implement the detectors by means of different devices for the detection of acoustic sound waves. As an example, optical sensors, in particular optical waveguides, may be used which are deformed by the impinging sound waves and thus cause the signals, which are guided through the optical waveguide, to change.

The excitation source can be in the form of a laser, with infrared lasers being particularly suitable.

As an alternative, the thermal excitation of the three-dimensional object can also be achieved by a microwave source.

In order to improve the sound propagation characteristics between object and detector, the at least one detector and the object are arranged advantageously in a liquid coupling medium. Distilled water or else mineral oil can be used as said liquid coupling medium.

For the purpose of its protection, the detector can be provided with a protective sheet. Care must be taken here that the sensitivity of the detector is not reduced by this protective sheet.

A stepping motor can be used as movement device for moving the at least one detector relative to the object or vice versa.

The reconstruction device is commonly in the form of a computer.

Finally, a display for displaying the image of the object can be provided.

Other features which are considered as characteristic for the invention are set forth in the appended claims.

Although the invention is illustrated and described herein as embodied in thermoacoustic tomographic method and thermoacoustic tomograph, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
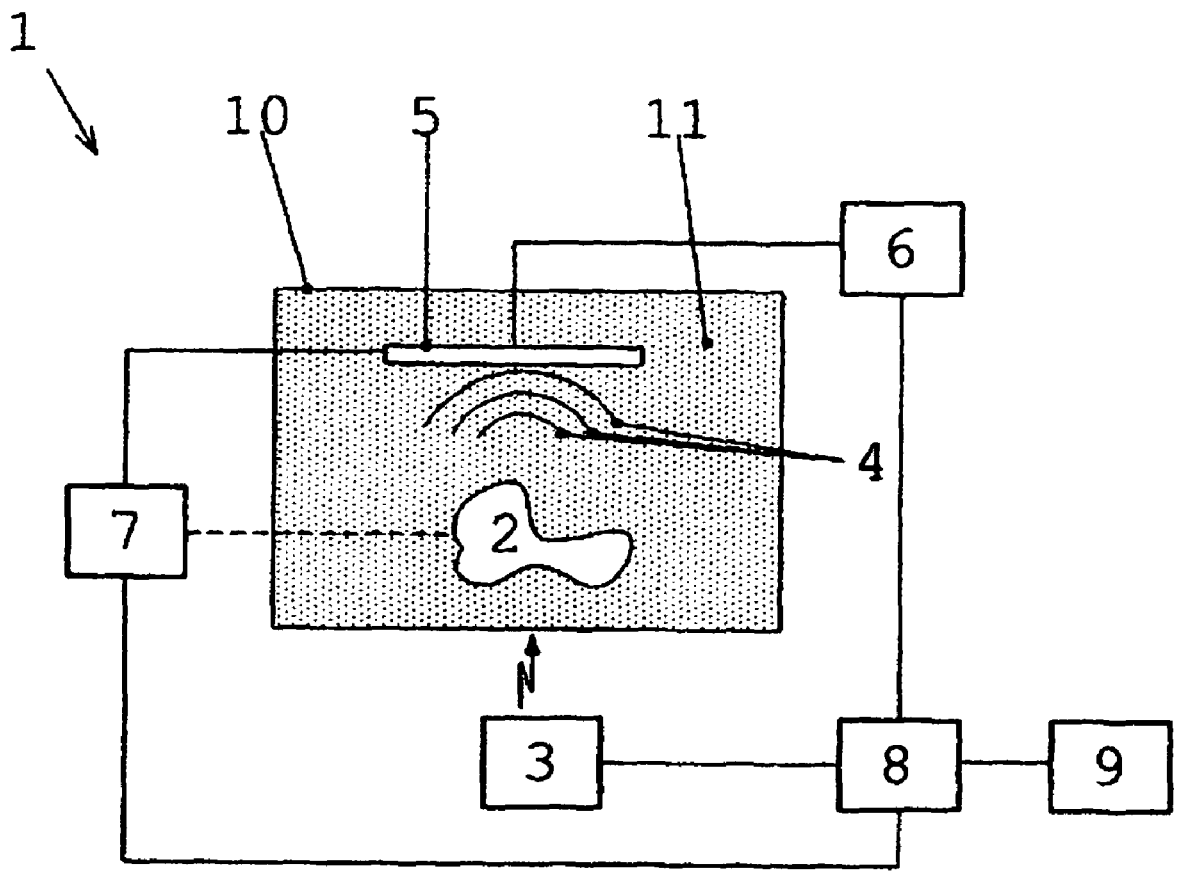
FIG. 1 is a block diagram of a thermoacoustic tomograph according to the present invention.

Referring now to the figures of the drawing in detail and first, particularly, to FIG. 1 thereof, there is shown a thermoacoustic tomograph 1 for imaging, for example, a three-dimensional object 2, for example a tissue sample. The object 2 is thermally excited by means of a source 3, for example a pulsed laser or a microwave source. The acoustic waves 4 caused by the object 2 by virtue of the thermal excitation are detected by a detector 5 and the detected signals are passed to an amplifier 6. In order to achieve a movement of the object 2 relative to the detector 5, a movement device 7, for example a stepping motor, is connected to the object 2 or to the detector 5. The signals originating from the amplifier 6 together with the control signals of the movement device 7 are passed to a device 8 for reconstructing the object 2. The reconstruction device 8 may, for example, be in the form of a corresponding computer device. At the same time, the excitation source 3 is also connected to the reconstruction device 8 in order to correspondingly control the thermal excitation. Finally, the reconstructed image of the object 2 can be displayed on a display 9. In order to improve the sound propagation characteristics from the object 2 to the detector 5, the object 2 and the detector 5 are arranged in a container 10 with a liquid coupling medium 11. The liquid coupling medium 11 can be in the form of distilled water or else a mineral oil having the best possible sound propagation speeds.

Figure 2:
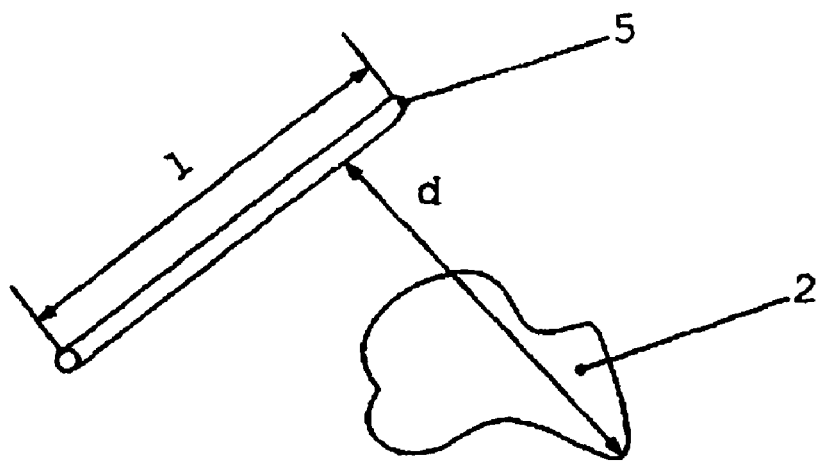
FIG. 2 is a diagram of a linear detector according to the present invention.

According to the invention, the detector 5 has a size of at least $\sqrt{8} \cdot d$ at least in one dimension, where d denotes the maximum distance from a point of the object 2 to be imaged to the detector 5 (see FIG. 2). A plurality of detectors 5 can, of course, also be arranged one next to another in order to reduce the recording time for the tomographic method (not illustrated).

If the object 2 is a two-dimensional object 2, a rotation about a single axis suffices. If a three-dimensional object 2 is examined, the detector 5 must be moved tangentially about the surface of the object 2 in all possible directions or, conversely, the object 2 must be moved in relation to the detectors 5. In order to reconstruct the object 2, various known, new, but also combinations of a wide variety of methods can be used. As an example, reference is made to the reconstruction described by Köstli and Beard (K.P. Köstli, P.C. Beard: Two-dimensional photoacoustic imaging by use of Fourier transform image reconstruction and a detector with an anisotropic response. Applied Optics, 42(10), 2003). When planar flat detectors 5 are used, the reconstruction can be effected in a particularly suitable manner and with little effort by means of the two-dimensional inverse Radon transformation.

FIG. 2 shows a perspective detail of the position of the detector 5 in relation to the object 2. The detector 5 is in the form of a linear detector, with the dimension I of the detector 5 in one dimension being at least $\sqrt{8} \cdot d$, where d denotes the maximum distance from a farthest point of the object 2 to be imaged to the detector 5.

Figure 3:
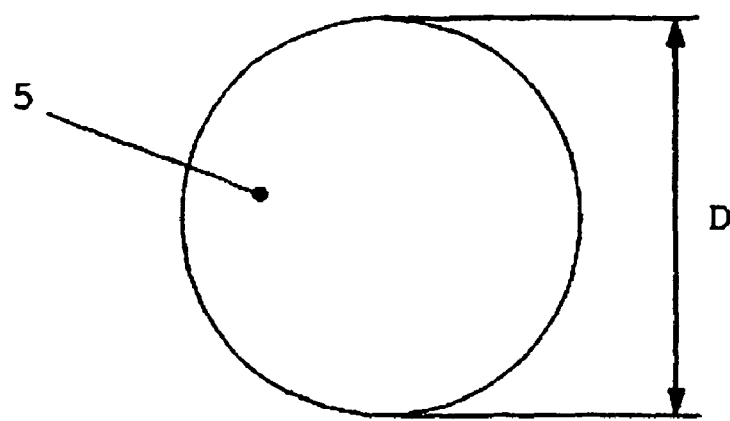
FIG. 3 shows a flat planar detector having a circular cross section.

FIG. 3 shows an embodiment variant of a detector 5 in the form of a flat planar detector of circular shape. The diameter D of the disc is at least $\sqrt{8} \cdot d$.

Figure 4:
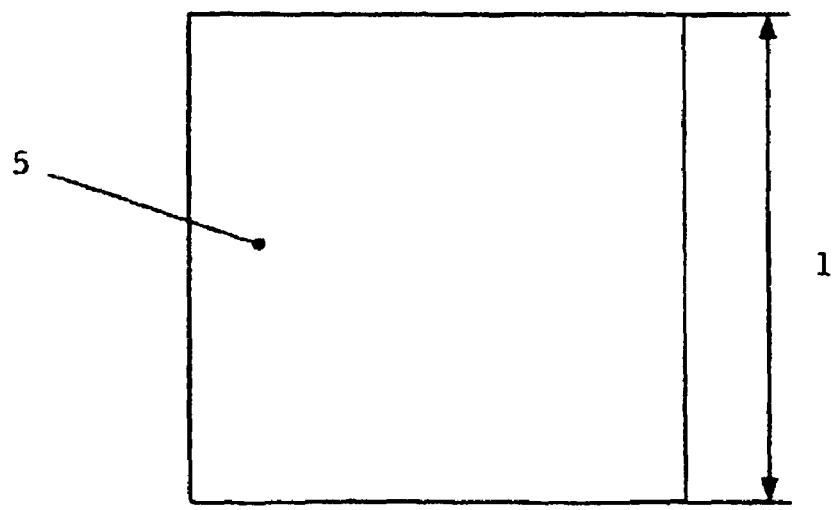
FIG. 4 shows a flat planar detector having a square cross section.

FIG. 4 shows a variant of a detector 5 in the form of a flat planar detector having a square cross section. The length I of the square is at least $\sqrt{8} \cdot d$.

Figure 5:
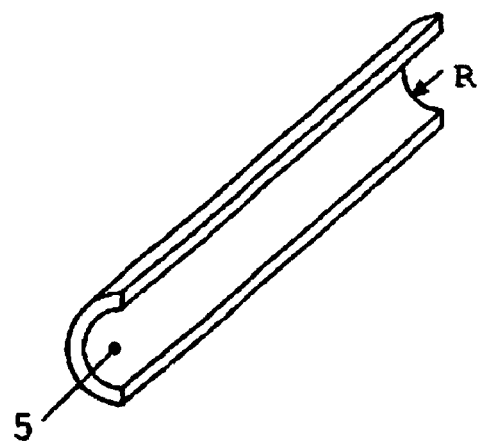
FIG. 5 is a perspective view of a concavely curved detector.

FIG. 5 shows a perspective view of a detector 5 having a curved shape, with the radius R of the curvature being capable of having various designs depending on the circumstances and also on the size of the object 2. The curvature of the detector 5 means that the external dimensions are smaller, which means that the detector 5 can be moved about the object 2 more easily. It will be understood, however, that the curvature must be taken into account in the reconstruction calculation.

Figure 6:
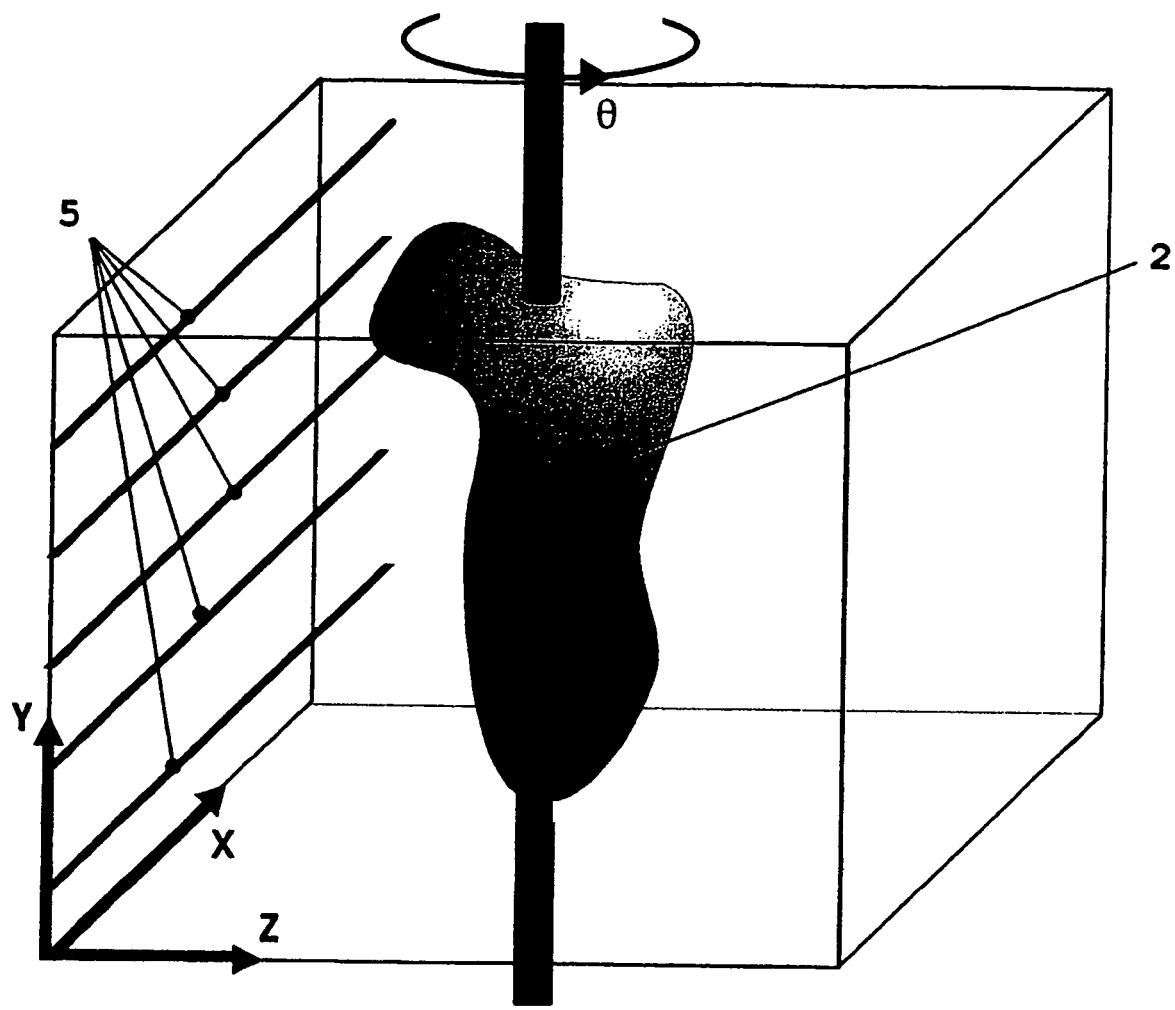
FIG. 6 is a perspective and diagrammatic view of the arrangement of a plurality of linear detectors in relation to a three-dimensional object to be imaged.

Finally, FIG. 6 shows the arrangement of a plurality of linear detectors 5 parallel with respect to one another at a distance from the object 2. In this embodiment, the object 2 is rotated, for example, about a fixed axis and the acoustic waves emanating from the object 2 are detected by the parallel detectors 5. For each rotation angle of the object 2, the acoustic sound pressure caused by the thermal excitation is recorded by the detectors 5 and finally the image of the object 2 is reconstructed from the data thus obtained.

The present method and the present device permit the reconstruction of particularly highly resolved images of objects using detectors, such as piezoelements or optical sensors having a high cut-off frequency. The thermoacoustic tomographic method opens up new possibilities, in particular in medicine, which could not be achieved using the prior art imaging methods.

We claim:

1. A thermoacoustic tomograph for imaging an object, comprising:
    at least one excitation source configured to thermally excite the object;
    at least one large-area or integrating line detector for detecting acoustic waves caused by the object upon excitation thereof by said source, said at least one detector having a size chosen in dependence on a distance between said detector and a point of the object that is furthest away from said detector, wherein d denotes the distance between said detector and a point of the object that is furthest away from said detector, and wherein said detector has at least one dimension with an extent of at least $\sqrt{8} \cdot d$;
    a movement device for moving the object and/or the at least one detector relative to one another; and
    a device connected to said detector for reconstructing an image of the object from the acoustic waves detected by said detector in dependence on a respective position of the object.

2. The tomograph according to claim 1, wherein said at least one detector is a linear detector or a strip-shaped detector having a length of at least $\sqrt{8} \cdot d$.

3. The tomograph according to claim 2, wherein said detector is one of a plurality of mutually parallel linear or strip-shaped detectors.

4. The tomograph according to claim 1, wherein said at least one detector is a flat detector, with a surface having a diameter of at least $\sqrt{8} \cdot d$.

5. The tomograph according to claim 1, wherein said at least one detector has a planar shape.

6. The tomograph according to claim 1, wherein said at least one detector is concavely curved.

7. The tomograph according to claim 6, wherein said at least one detector has a semi-cylindrical shape.

8. The tomograph according to claim 1, wherein said detector has an upper cut-off frequency of several GHz.

9. The tomograph according to claim 1, wherein said at least one detector is a piezoelectric sensor.

10. The tomograph according to claim 9, wherein said at least one detector is a polyvinylidene fluoride sheet or layer.

11. The tomograph according to claim 9, wherein said at least one detector is a zinc oxide sheet or layer.

12. The tomograph according to claim 1, wherein said at least one detector is an optical sensor.

13. The tomograph according to claim 12, wherein said at least one detector is an optical waveguide.

14. The tomograph according to claim 1, wherein said at least one excitation source is a laser.

15. The tomograph according to claim 14, wherein said laser is an infrared laser.

16. The tomograph according to claim 1, wherein said at least one excitation source is a microwave source.

17. The tomograph according to claim 1, wherein said at least one detector and the object are commonly disposed in a liquid coupling medium.

18. The tomograph according to claim 1, wherein said at least one detector is provided with a protective sheet.

19. The tomograph according to claim 1, wherein said movement device is a stepping motor.

20. The tomograph according to claim 1, wherein said reconstruction device is a computer.

21. The tomograph according to claim 1, which comprises a display connected to said reconstruction device for displaying the image of the object.

\* \* \* \* \*

UNITED STATES PATENT AND TRADEMARK OFFICE
CERTIFICATE OF CORRECTION

PATENT NO. : 7,798,705 B2  Page 1 of 1
APPLICATION NO. : 11/647890
DATED : September 21, 2010
INVENTOR(S) : Peter Burgholzer et al.

It is certified that error appears in the above-identified patent and that said Letters Patent is hereby corrected as shown below:

Title Page, Item (73) Assignee should read as follows:

(73) Assignee: Upper Austrian Research GmbH, Linz (AT);
Universität Wien, Wien (AT)

Signed and Sealed this
Fourth Day of January, 2011

David J. Kappos
*Director of the United States Patent and Trademark Office*